United States Patent [19]

Yokoi

[11] Patent Number: 4,779,624
[45] Date of Patent: Oct. 25, 1988

[54] ULTRASONIC ENDOSCOPE

[75] Inventor: Takeshi Yokoi, Tokyo, Japan

[73] Assignee: Olympus Optical Co., Ltd., Tokyo, Japan

[21] Appl. No.: 50,498

[22] Filed: May 13, 1987

[30] Foreign Application Priority Data

May 21, 1986 [JP] Japan .................. 61-116671

[51] Int. Cl.⁴ .................. A61B 1/06; A61B 10/00
[52] U.S. Cl. .................. 128/660.06; 128/6; 128/660.03
[58] Field of Search .................. 128/660, 4, 5, 6, 7, 128/8

[56] References Cited

U.S. PATENT DOCUMENTS

| | | | |
|---|---|---|---|
| 3,643,653 | 2/1972 | Takahashi et al. | 128/6 |
| 3,924,608 | 12/1975 | Mitsui | 128/6 |
| 4,408,598 | 10/1983 | Ueda | 128/4 |
| 4,433,692 | 2/1984 | Baba | 128/660 |
| 4,509,507 | 4/1985 | Yabe | 128/4 |
| 4,567,880 | 2/1986 | Goodman . | |

FOREIGN PATENT DOCUMENTS 0029556  3/1981  European Pat. Off. ......... 128/4
58-65148  4/1983  Japan .

Primary Examiner—Francis Jaworski
Assistant Examiner—George Manuel
Attorney, Agent, or Firm—Frishauf, Holtz, Goodman & Woodward

[57] ABSTRACT

This invention relates to an ultrasonic endoscope which includes a manipulating portion coupled to a light source device and an ultrasonic observation apparatus through a universal cord, an insertion portion inserted in a body cavity, and a sub-manipulating portion arranged between the insertion portion and the manipulating portion, an air-supply path and a suction path being arranged in the universal cord, the insertion portion having a distal end portion on which an observation optical system and an ultrasonic vibrator are mounted, the ultrasonic vibrator being covered with a balloon fixed to a surrounding portion of the distal end portion, and an optical system water-supply pipe for supplying water for washing the observation optical system and a balloon water-injection pipe for injecting water into the balloon being arranged in the insertion portion. The ultrasonic endoscope of this invention is provided with a water path switch means capable of causing the water-supply path in the universal cord to communicate with one or both of the optical system water-supply pipe and the balloon water-injection pipe in the insertion portion.

11 Claims, 7 Drawing Sheets

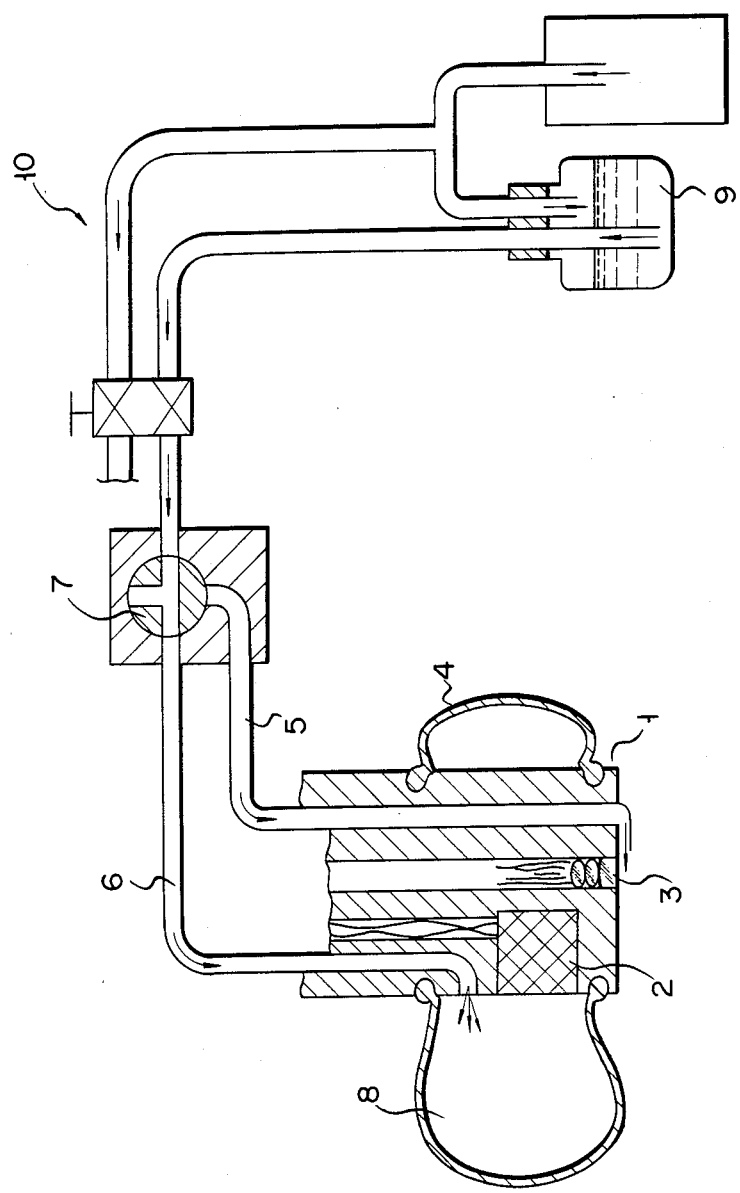
F I G. 3

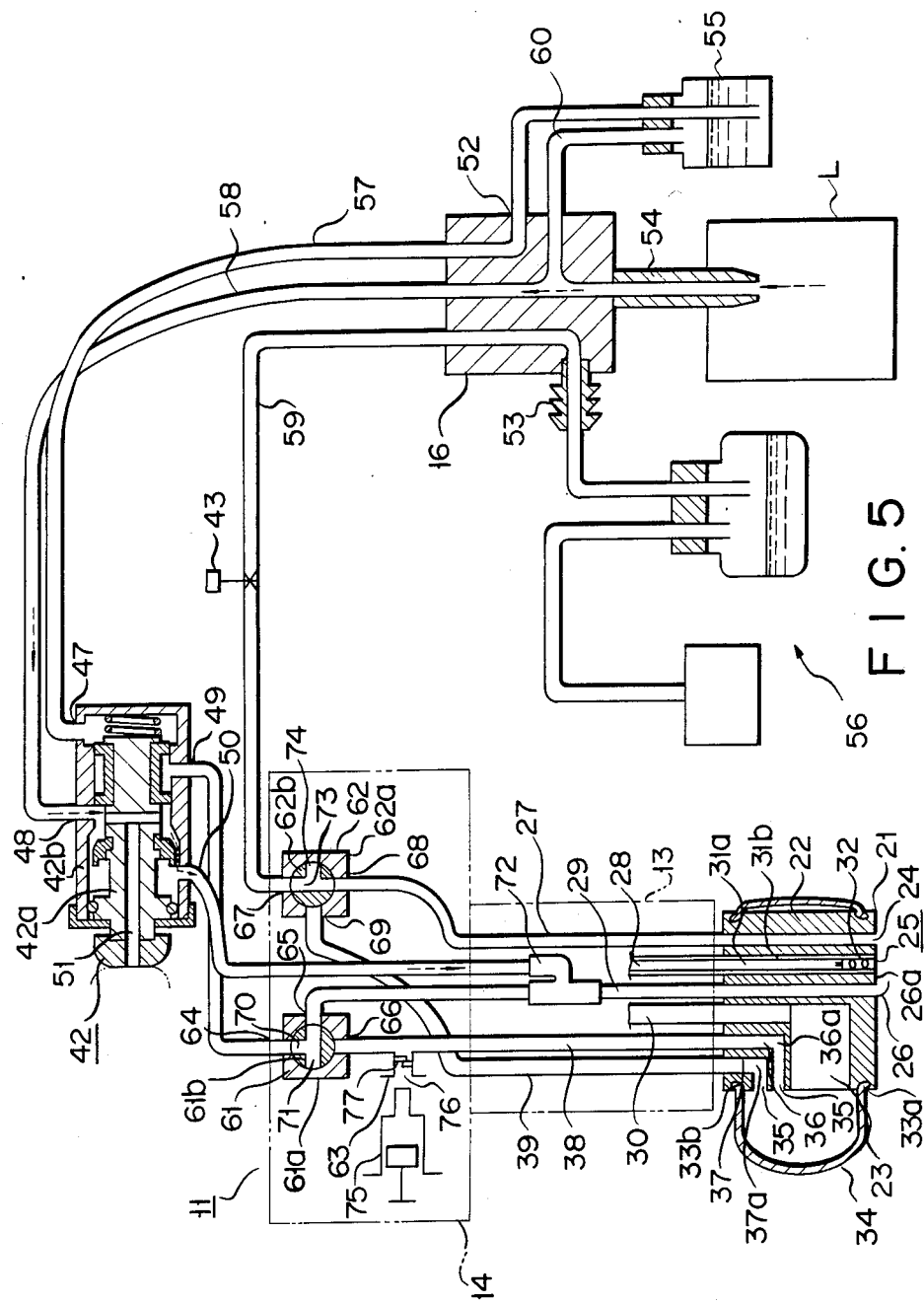
F I G. 5

4,779,624

ULTRASONIC ENDOSCOPE

BACKGROUND OF THE INVENTION

The present invention relates to an ultrasonic endoscope incorporating an ultrasonic vibrator in a hard distal end portion thereof.

In general, an ultrasonic endoscope is known which incorporates an ultrasonic vibrator for transmitting and receiving ultrasonic waves in a hard distal end portion of an insertion portion of the endoscope. The ultrasonic endoscope can obtain a tomographic image in the depth direction of, e.g., a body cavity wall by ultrasonic waves transmitted or received through the ultrasonic vibrator in the hard distal end portion. When the ultrasonic endoscope scans the ultrasonic waves using the ultrasonic vibrator in the hard distal end portion to obtain a tomographic image of the opposing wall, a better tomographic image with less attenuation can be obtained if the ultrasonic waves are scanned not through an air gap but through a liquid.

For this reason, various conventional ultrasonic endoscopes have been developed, and the typical one is disclosed in Japanese Patent Disclosure (Kokai) No. 58-65148.

As shown in FIGS. 1 and 2, conventional ultrasonic endoscope a disclosed in Japanese Patent Disclosure (Kokai) No. 58-65148 has manipulating portion f used by an operator such as a doctor, and insertion portion g extending from manipulating portion f and inserted in a body cavity. Hard portion b is coupled to the distal end of insertion portion b through soft portion k and bent portion l. Ultrasonic vibrator c is mounted on the outer surface of hard portion b, and an observation optical system is mounted on the distal end face thereof. Ultrasonic vibrator c mounted on the outer surface of hard distal end portion b is covered with balloon d, two ends of which are fixed.

A water-supply path for supplying washing water for washing the observation optical system and water injection path e for injecting water into balloon d extend in insertion portion g of endoscope a therealong. After water is injected into balloon d through path e, ultrasonic waves are scanned to the opposing wall through the water in balloon d.

Endoscope connector n and electrical connector p are mounted on distal ends of universal cord m and signal cable o connected to manipulating portion f, respectively. Connector n is coupled to an ultrasonic wave observation apparatus, and connector n is connected to a light source. Connector p is coupled, through an appropriate tube, to a water-supply tank arranged in a separate location, and water is supplied to the watersupply path for the washing water of the observation optical system.

Sub-manipulating portion h is coupled between manipulating portion f and insertion portion g. Portion h is provided with liquid supply port i and suction manipulation valve j. Upon operation of vibrator c, a liquid supply syringe is coupled to port i of portion h, and water is injected from the syringe into balloon d sequentially through port i and path e. Note that reference symbol q denotes a balloon suction hole; and r, a suction port formed in endoscope connector n.

In the conventional ultrasonic endoscope, the water-supply syringe must be coupled to liquid-supply port i of sub-manipulating portion h upon operation of ultrasonic vibrator c, and water must be injected from the syringe into balloon d sequentially through port i and path e. Therefore, during the use of endoscope a, the syringe must be mounted on port i of portion h, and must be manually operated, resulting in cumbersome operation and poor operability.

Another arrangement can be considered wherein a liquid supply pipe coupled to an automatic liquid supply pump is coupled to liquid supply port i of submanipulating portion h, and water is automatically injected into balloon d sequentially through port i and path e by the pump. In this case, however, the liquid supply pipe coupled to port i may interfere with the operation of endoscope a, and poses a problem on an improvement of operability.

It is an object of the present invention to solve the above problems.

It is another object of the present invention to provide an ultrasonic endoscope with improved operability.

It is still another object of the present invention to provide an ultrasonic endoscope which can facilitate washing of an observation optical system and water injection into a balloon.

SUMMARY OF THE INVENTION

In order to achieve the above objects, the ultrasonic endoscope of the present invention includes a water path switching means which can communicate a water-supply path in a universal cord with one or both of an optical system water-supply pipe in an insertion portion and a balloon water injection pipe.

The ultrasonic endoscope of the present invention can omit a cumbersome operation such that a liquid-supply syringe is coupled to a liquid-supply port of a sub-manipulating portion and the liquid-supply syringe is operated to inject water into the balloon during use of the conventional ultrasonic endoscope.

According to the present invention, an observation optical system can be very easily washed or water can be easily injected into the balloon by utilizing the water path switching means.

Other features and advantages of the present invention will be apparent from the following description of the embodiment taken in conjunction with the accompanying drawings.

BRIEF DESCRIPTION OF THE DRAWINGS

FIG. 3 is a diagram of an ultrasonic endoscope according to a first embodiment of the present invention;

FIG. 5 illustrates internal piping of the ultrasonic endoscope shown in FIG. 4;

DESCRIBED DESCRIPTION OF THE PREFERRED EMBODIMENTS

Figures 1, 2:
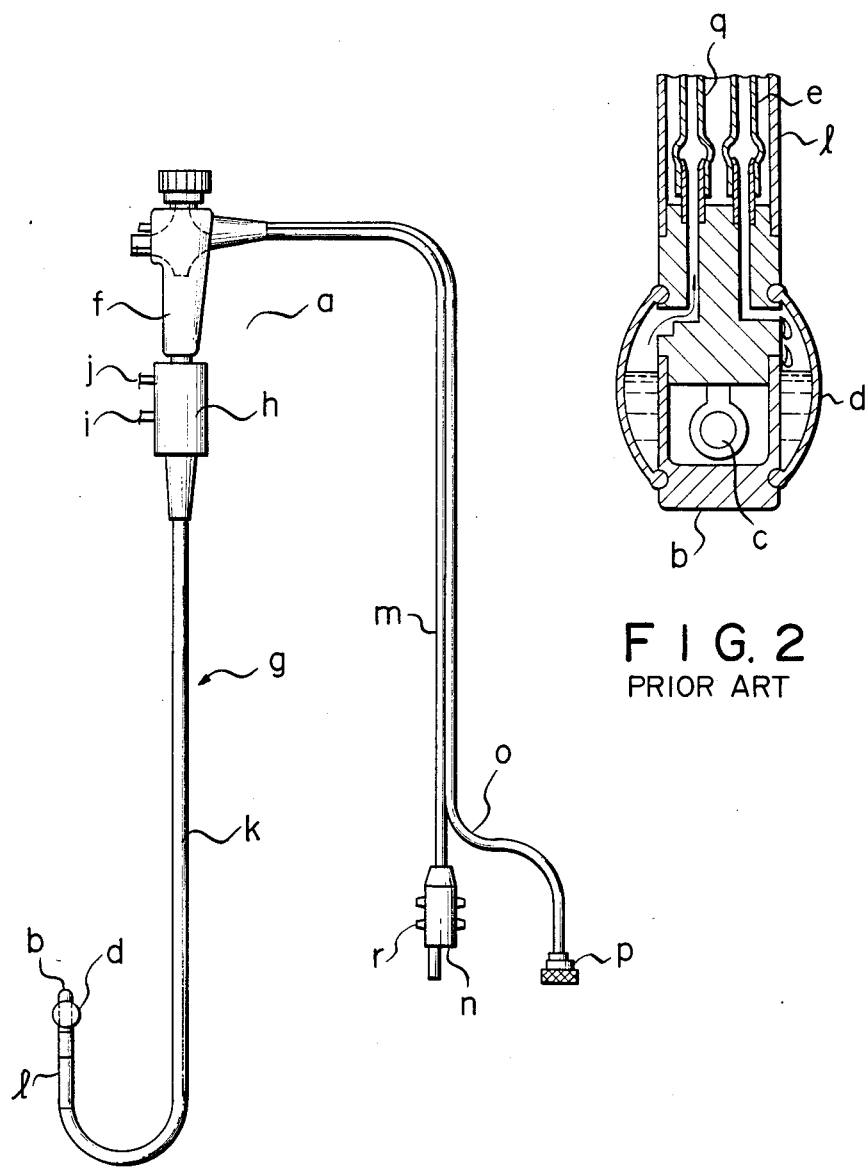
FIG. 1 schematically shows an outer appearance of a conventional ultrasonic endoscope.
FIG. 2 is a longitudinal sectional view of a hard distal end portion of the ultrasonic endoscope shown in FIG. 1.

An ultrasonic endoscope for carrying out the present invention will now be described with reference to FIG. 3.

Ultrasonic endoscope 10 shown in FIG. 3 is a simplest example for embodying the principle of the present invention.

Ultrasonic endoscope 10 has distal end portion 1, on which ultrasonic vibrator 2 and observation optical system 3 are mounted, at a far end portion of an insertion portion extending from a manipulating portion (not shown).

Ultrasonic vibrator 2 is mounted on the outer surface of distal end portion 1, and the outer surface of vibrator 2 is covered with balloon 4. The two ends of balloon 4 are tightly fixed to the outer surface of distal end portion 1 by an appropriate technique, and gap 8 is formed between balloon 4 and distal end portion 1. Optical system water-supply pipe 5 for supplying washing water for washing optical system 3 is open to observation optical system 3. Balloon water-injection pipe 6 for supplying water into gap 8 between balloon 4 and vibrator 2 on the outer surface of distal end portion 1 is open to gap 8.

Water path switching means 7 is arranged in water-supply pipe 5 for washing the observation optical system. Switching means 7 comprises a three-way cock, and can be selectively switched by a proper control means between a balloon water-injection position at which balloon water-injection pipe 6 communicates with water tank 9, as shown in FIG. 3, and an optical system washing position at which water tank 9 communicates with water-supply pipe 5.

Therefore, according to ultrasonic endoscope 10 shown in FIG. 3, since water path switching cock 7 can be selectively switched between the optical system washing position at which water is supplied to water-supply pipe 5 for the washing water and the balloon water-injection position at which water is supplied to balloon water-injection pipe 6, water in tank 9 which is supplied to pipe 5 for the washing water can be easily supplied to pipe 6 by simple switching cock 7.

Figure 4:
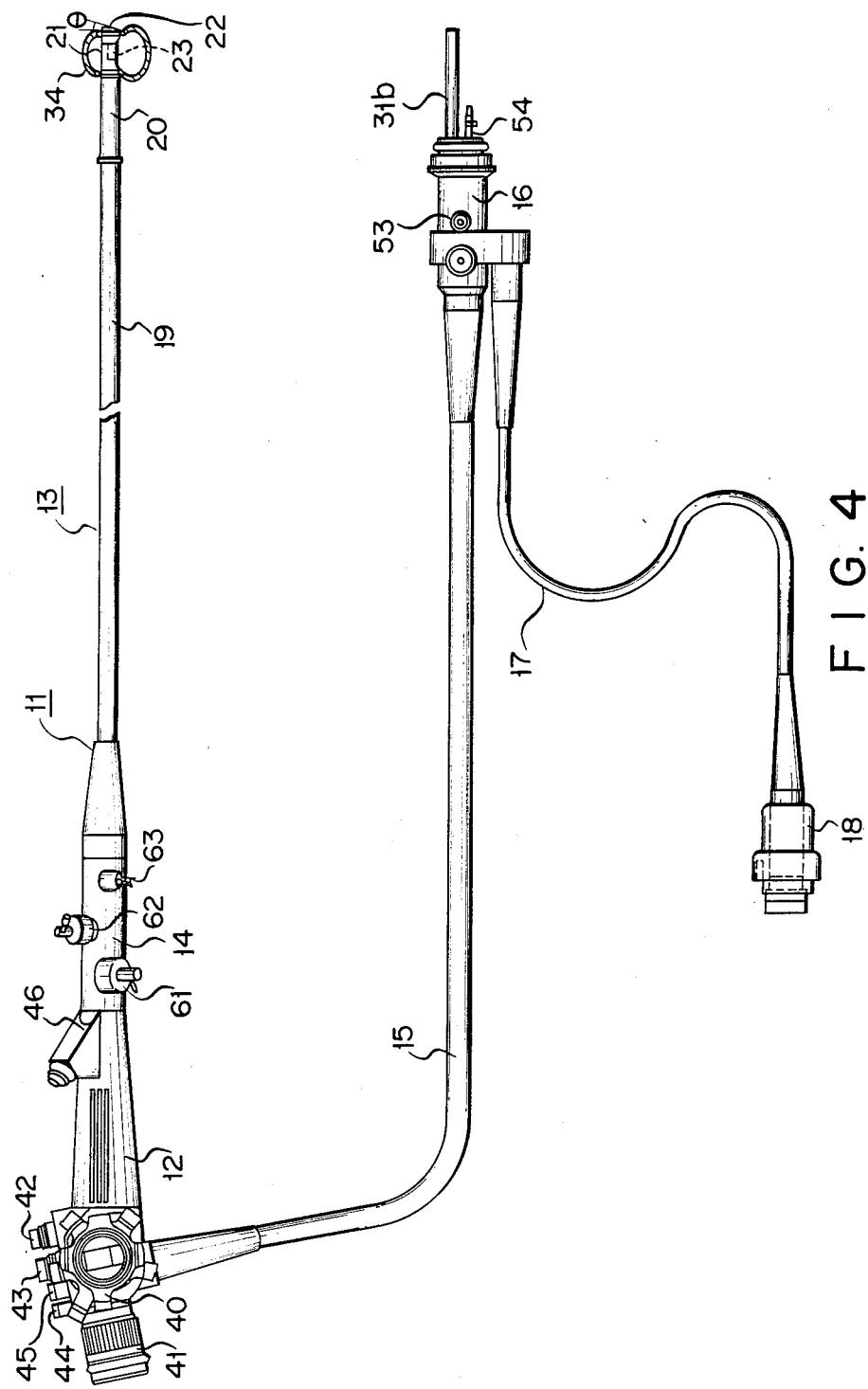
FIG. 4 shows a partially cutaway outer appearance of an insertion portion of an ultrasonic endoscope according to a second embodiment of the present invention.

FIG. 4 shows a detailed embodiment of an ultrasonic endoscope to which the present invention is applied.

The overall ultrasonic endoscope is denoted by reference numeral 11. Ultrasonic endoscope 11 has manipulating portion 12, insertion portion 13 to be inserted in a body cavity and sub-manipulating portion 14 arranged between portions 12 and 13.

Insertion portion 13 to be inserted in a body cavity is constituted by flexible soft portion 19 extending from sub-manipulating portion 14, flexible portion 20, and distal end portion 21. Ultrasonic vibrator array 23 is mounted on the outer surface of distal end portion body 22 of distal end portion 21. The distal end face of distal end portion body 22 is formed to be inclined at predetermined angle $\theta$ (about 15 degrees) with respect to a direction perpendicular to the axial direction.

Bend adjusting knob 40 for adjusting a bending state of flexible portion 20 of insertion portion 13, eyepiece 41 for allowing optical observation, air-supply/water-supply valve 42, and suction valve 43 are arranged on manipulating portion 12. Release switch 44 for remote-controlling equipment such as a camera, freeze switch 45 for freezing an image displayed on a TV monitor of an ultrasonic observation apparatus, and the like are arranged near valves 42 and 43. Treatment tool insertion port 46 is open to a portion near submanipulating portion 14.

Water-supply switching cock (water path switching means) 61, suction switching cock 62, and syringe mount port 63 are disposed on sub-manipulating portion 14.

Endoscope connector 16 is mounted on the distal end of universal cord 15 extending from manipulating portion 12. Water-supply port 52, suction port 53, electrical contacts, and the like are mounted on the outer surface of connector 16. A connecting end portion of light-guide portion 31b of optical fibers 28 and air-supply pipe 54 project from the distal end face of endoscope connector 16.

Figure 6:
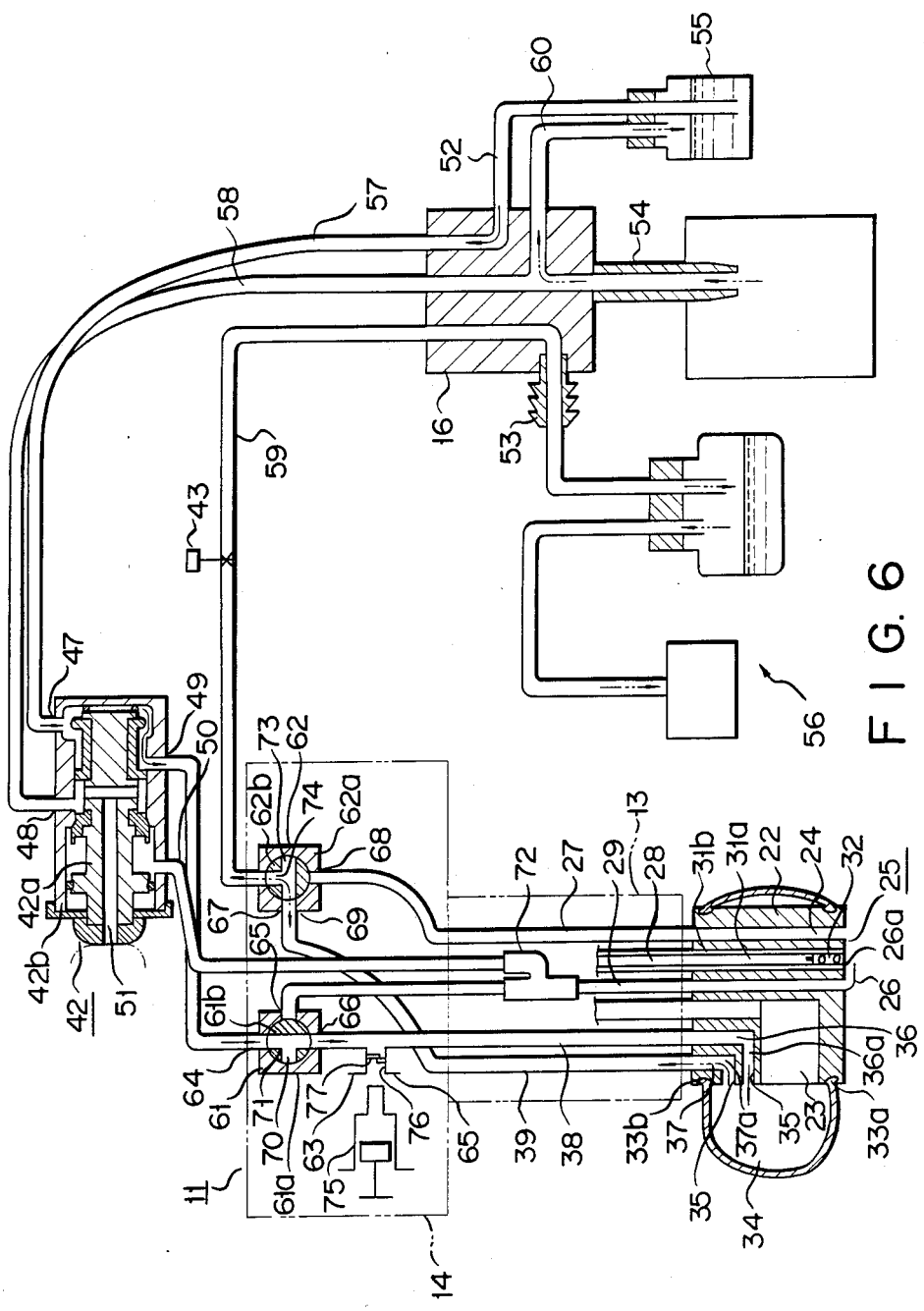
FIG. 6 is a diagram for explaining a state of water injection into a balloon of the endoscope, and is a longitudinal sectional view of a sub-manipulating portion of the ultrasonic endoscope according to the present invention.

As shown in FIGS. 5 and 6, in a state wherein endoscope connector 16 is coupled to light source device L, light-guide portion 31b is optically connected to a light source of light source device L through the connecting end portion, and air-supply pipe 54 is connected to an air-supply mechanism in device L. Water-supply port 52 is coupled to water-supply tank 55 through an appropriate tube, and suction plug 53 is connected to suction device 56 through an appropriate tube. Port 52 communicates with water inlet port 47 of valve 42 through water-supply path 57 extending in universal cord 15. Suction plug 53 communicates with an outlet port of suction valve 43 through suction path 59 in universal cord 15. One end of branch pipe 60 is coupled to airsupply path 58 in universal cord 15, and the other end of pipe 60 is inserted in water-supply tank 55.

The internal structure of ultrasonic endoscope 11 shown in FIG. 4 will now be described with reference to FIG. 5.

Suction-forceps port 24, air-supply/water-supply nozzle 26, and observation optical system 25, whose distal end face is located between port 24 and nozzle 26, are disposed on the distal end face of distal end portion body 22 of distal end portion 21 of insertion portion 13.

Treatment tool insertion channel 27, liquid guide/image guide optical fiber bundle 28, air-supply/water-supply pipe 29, and bundle 30 of signal cables (Al-shielded lines) for ultrasonic vibrator 23 are arranged inside insertion portion 13.

Nozzle 26 arranged at the distal end face of body 22 communicates with pipe 29. Nozzle 26 is arranged so that its spray orifices 26a are directed toward the distal end face of observation optical system 25. Water or air supplied through pipe 29 is sprayed toward the distal end face of observation optical system 25 from orifices 26a of nozzle 26.

Light guide/image guide optical fiber bundle 28 constituting optical system 25 has image-guide portion 31a and light-guide portion 31b arranged on the outer surface of portion 31a in a ring form. In bundle 28, objective lens 32 is arranged to face the distal end of image-guide portion 31a, and the distal end portion of light-guide portion 31b of bundle 28 extends to the outer peripheral position of objective lens 32. Light transmitted through portion 31b of bundle 28 is emerged from the distal end face of portion 31b toward the mounting surface of ultrasonic vibrator 23 to be inclined at predetermined angle $\theta$ (about 15 degrees) with respect to a direction perpendicular to the axial direction of body 22.

Balloon mounting grooves 33a and 33b are formed on the outer surface of body 22 along its circumferential direction. O-ring portions formed on the two end portions of balloon 34 made of an elastic material such as rubber having flexibility are respectively fitted in grooves 33a and 33b, so that balloon 34 covers the overall outer surface of body 22.

Two communication grooves 35 are formed in the outer surface of body 22 between the mounting portion of vibrator 23 and groove 33b along the circumferential direction. Grooves 35 respectively communicate with balloon water-injection hole 36 formed in the proximal end portion side of body 22 and balloon suction hole 37 having the same structure as that of hole 36. Hole 36 communicates with balloon water-injection pipe 38, and hole 37 communicates with balloon suction pipe 39.

Air-supply/water-supply valve 42 provided to manipulating portion 12 will be described below.

Valve 42 has stepped piston 42a which is slidable in the axial direction inside an inner hole of valve body 42b. Water inlet port 47, air inlet port 48, water outlet port 49, and air outlet port 50 are formed in valve body 42b. Air vent hole 51 open to an external portion is formed in piston 42a.

FIG. 5 illustrates a state wherein piston 42a of valve 42 projects at a normal position. In this state, port 47 is disconnected from port 49, and port 48 communicates with port 50. Vent hole 51 of piston 42a communicates with an air path in valve body 42b. Therefore, hole 51 communicates with ports 48 and 50. If hole 51 is closed by, e.g., a finger of an operator, air cannot be spilt, and is flowed into pipe 29.

In a state wherein piston 42a is pushed in valve body 42b as shown in FIG. 6, port 48 is disconnected from port 50, and port 47 communicates with port 49.

Therefore, valve 42 can be selectively switched between the normal position at which air is spilt from manipulating portion 12, an air-supply position at which air is supplied to pipe 29 in insertion portion 13, and a water-supply position at which air is supplied to water-supply tank 55 to compress the interior of tank 55, so that water from tank 55 communicates with water-supply switching cock 61.

More specifically, at the normal position, piston 42a of valve 42 is located at a position shown in FIG. 5, and the finger of the operator is released from the head portion of piston 42a, so that vent hole 51 is open to air. At the normal position, air supplied from the air supply source in light source device L is supplied to manipulating portion 12 through connector 16 and universal cord 15, and is externally exhausted from through hole 51. At the air-supply position, vent hole 51 of valve 42 is closed by the finger of the operator. Therefore, air supplied from the air supply source in device L through connector 16 and path 58 in cord 15 to manipulating portion 12 is supplied to pipe 29 in insertion portion 13 through ports 48 and 50.

At the water-supply position, vent hole 51 of valve 42 is closed by the finger of the operator, and piston 42a is pushed in valve body 42b, so that air-supply path 58 in universal cord 15 is closed by piston 42a. Air from the air supply source is introduced, through branch path 60 of air-supply path 58, into water-supply tank 55 connected to water-supply port 52 of connector 16, thereby compressing the interior of water-supply tank 55. Then, water is supplied under pressure from water-supply tank 55 to water-supply path 57 of universal cord 15, and is then supplied to pipe 29 side in insertion portion 13 through ports 47 and 49 of valve 42.

Inlet and outlet ports are formed in a valve body of suction valve 43 in a known manner. At a normal position at which a piston of valve 43 projects, the inlet port is disconnected from the outlet port, and in a state wherein the piston of valve 43 is pushed in, the inlet and outlet ports communicate with each other.

Coupling member 72 is interposed between second port 65 of water-supply switching cock 61 and pipe 29, so that pipe 29 communicates with port 50 of valve 42 through coupling member 72.

Suction switching cock 62 and syringe mount port 63 provided to sub-manipulating portion 14 will be explained below.

Figure 7:
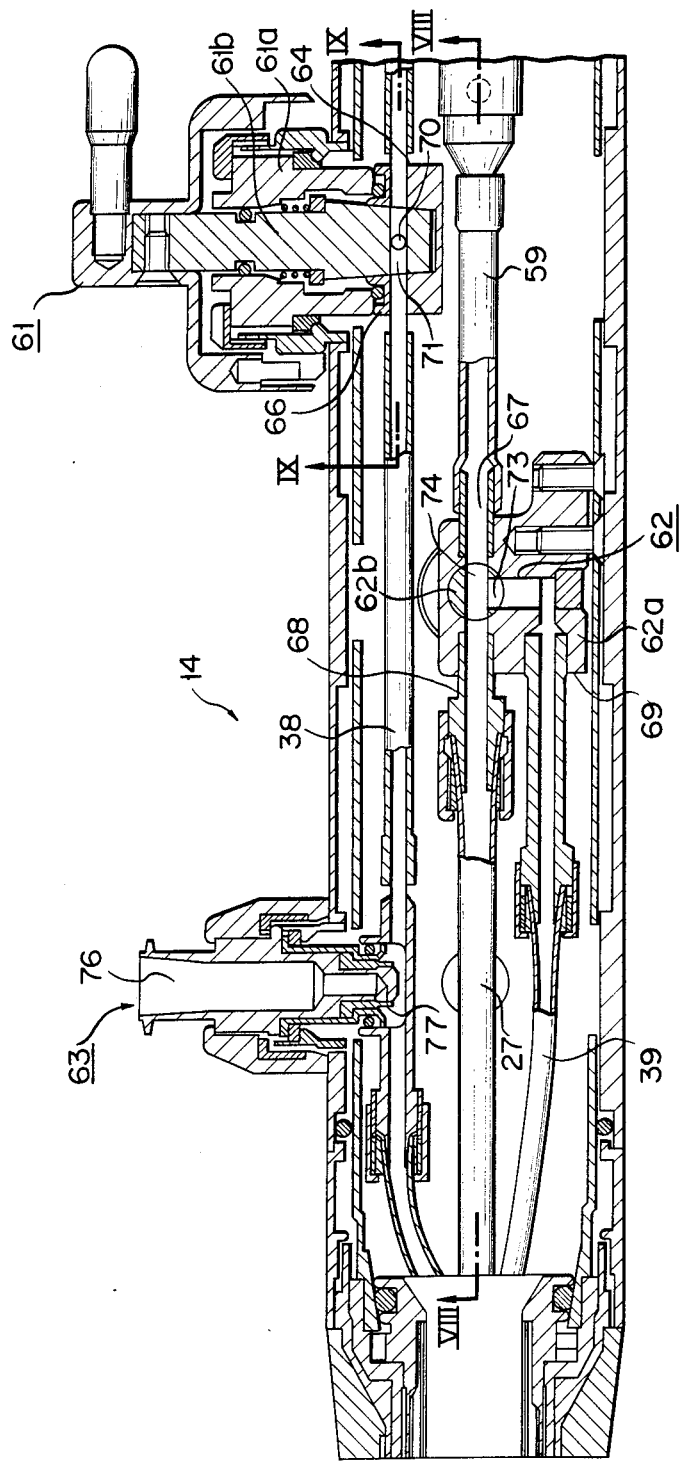
FIG. 7 is a longitudinal sectional view of the sub-manipulating portion of the ultrasonic endoscope shown in FIG. 4.

As shown in FIGS. 5 and 6, water-supply switching cock 61 is formed to have cock body 61a and pivotal member 61b pivotally mounted in cock body 61a, and FIG. 7 shows its structure in more detail.

First, second, and third ports 64, 65, and 66 are provided to cock body 61a of cock 61. First port 64 of cock 61 communicates with outlet port 49 of valve 42. Second port 65 communicates with pipe 29. Third port 66 communicates with water-injection pipe 38. First and second paths 70 and 71 communicating with path 70 are formed in pivotal member 61b of cock 61. Cock body 61a can be selectively switched between an optical system washing position shown in FIG. 5, a balloon water-injection position shown in FIG. 6, and a washing/water-injection position shown in FIGS. 7 and 9.

At the optical system washing position of cock 61 shown in FIG. 5, first and second ports 64 and 65 communicate with each other through first path 70 of cock body 61a, and third port 66 is disconnected. At the balloon water-injection position shown in FIG. 6, first and third ports 64 and 66 communicate with each other through second path 71, and second port 65 is disconnected. Furthermore, at the washing/water-injection position shown in FIG. 7 and particularly in FIG. 9, first, second, and third ports 64, 65, and 66 communicate with each other through first and second paths 70 and 71.

Figures 8, 9:
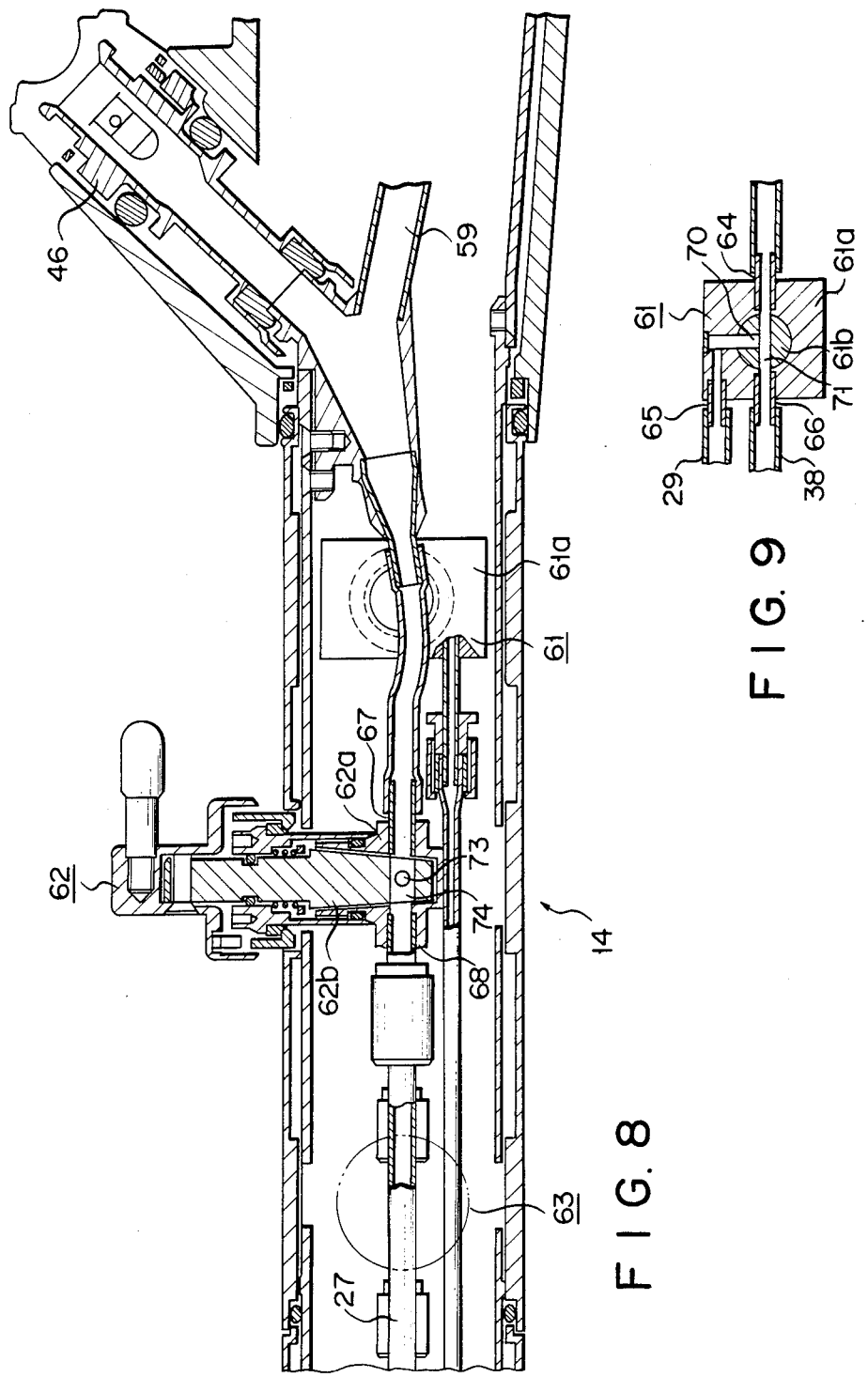
FIG. 8 is a sectional view taken along a line VIII—VIII in FIG. 7.
FIG. 9 is a sectional view taken along a line IX—IX in FIG. 7.

Similarly, as shown in FIGS. 5 and 6, suction switching cock 62 has a structure comprising cock body 62a and pivotal member 62b pivotally mounted in cock body 62a, and FIG. 8 shows its structure in more detail.

Fourth, fifth, and sixth ports 67, 68, and 69 are formed in cock body 62a of suction switching cock 62. Fourth port 67 communicates with the inlet port of suction valve 43, fifth port 68 communicates with channel 27, and sixth port 69 communicates with balloon suction pipe 39. Third and fourth paths 73 and 74 communicating with path 73 are formed in pivotal member 62b of cock 62. Pivotal member 62b can be selectively switched between the body cavity suction position shown in FIG. 5, the balloon suction position shown in FIG. 6, and the double suction position shown in FIGS. 7 and 8.

At the body cavity suction position of cock 62 shown in FIG. 5, fourth an fifth ports 67 and 68 communicate with each other through third path 73, and sixth port 69 is disconnected. When member 62b is pivoted to the balloon suction position shown in FIG. 6, fourth and sixth ports 67 and 69 communicate with each other through fourth path 74, and fifth port 68 is disconnected. Furthermore, at the double suction position shown particularly in FIG. 7, fourth, fifth, and sixth paths 67, 68, and 69 communicate with each other through third and fourth paths 73 and 74.

As shown in FIGS. 5 to 7, syringe mount port 63 is provided in balloon water-injection pipe 38. Port 63 comprises syringe receiving portion 76 for receiving syringe 75 and check vale 77 arranged between portion 76 and pipe 38. When syringe 75 is inserted in portion 76, water can be manually injected into balloon 34. Check valve 77 is normally held in a closed state, and can cause water to flow from syringe 75 toward pipe 38 in accordance with a water-supply pressure from syringe 75 fitted in portion 76.

A stock cock which can communicate with or be disconnected from an external portion may be arranged between syringe receiving portion 76 and balloon water-injection pipe 38 in place of check valve 77 provided to syringe mount port 63.

The stop cock may be detachably arranged on syringe receiving portion 76. In this case, check valve 77 can be omitted from a portion between syringe receiving portion 76 and balloon water-injection pipe 38.

Ultrasonic endoscope 11 of the present invention is used as follows.

Endoscope connector 16 is connected to light source device L, and water-supply port 52 thereof is coupled to water-supply tank 55. Suction port 53 is coupled to suction device 56 through an appropriate tube. Insertion portion 13 of endoscope 11 is inserted in a body cavity, and distal end portion 21 is guided to a portion near a target portion.

In a normal state, since vent hole 51 formed in piston 42a of valve 42 is open to air, air supplied from the air supply source of device L is released in the atmosphere, and no pressure is applied to the interior of water tank 55. Therefore, neither air nor water can be supplied to insertion portion 13.

When optical system 25 is to be washed, cock 61 is switched to the optical system washing position as shown in FIG. 5 to cause first and second ports 64 and 65 to communicate with each other, and cock 62 is switched to the body cavity suction position to cause fourth and fifth ports 67 and 68 to communicate with each other. Thereafter, suction valve 43 is set at the suction position, and vent hole 51 of piston 42a of valve 42 is pushed by a finger to disconnect port 48 from port 50, and to cause port 47 and port 49 to communicate with each other.

The interior of water tank 55 is compressed, and water therein is supplied to water-supply port 52 through an appropriate tube. Then, water is sprayed toward the surface portion of observation optical system 25 from spray orifices 26a of nozzle 26 through path 57, valve 42, cock 61, and pipe 29. Water inside the body cavity is drawn by suction device 56 from suction-forceps port 24 through cock 62, valve 43, and suction path 59.

When water is injected into balloon 34, pivotal member 61b of cock 61 is switched to the balloon water-injection position, and pivotal member 62b of cock 62 is switched to the balloon suction position. Thereafter, hole 51 of valve 42 of manipulating portion 12 is similarly closed, and piston 42a is pushed in. Then, the piston of valve 43 is pushed in to switch it to the suction position.

The interior of water tank 55 is compressed by air from branch pipe 60. Water inside tank 55 is supplied to cock 61, and is filled in balloon 34 from cock 61 through pipe 38, hole 36, port 36a, and groove 35. Air inside balloon 34 is drawn by suction device 56 from the other groove 35 sequentially through port 37a, hole 37, and pipe 39.

Thereafter, ultrasonic vibrator 23 is operated to obtain a desired tomographic image of an opposing wall.

As shown in FIGS. 7 to 9, cock 61 is switched to the washing/water-injection position, cock 62 is switched to the double suction position, and valves 42 and 43 can be operated as described above. In this state, water can be supplied to both optical system 25 and balloon 34, and air or water in the body cavity or balloon can be drawn at the same time.

According to the ultrasonic endoscope described above, a cumbersome operation such that a liquid-supply syringe is coupled to a liquid-supply port of submanipulating portion 14 during use of endoscope 11, and the syringe is manually operated to inject water into balloon 34 can be omitted. For this reason, the endoscope of the present invention can be easy to operate.

Water-supply path 57 is arranged in universal cord 15, air-supply/water-supply valve 42 is arranged on manipulating portion 12, and water-supply switching cock 61 and suction switching cock 62 are arranged on submanipulating portion 14. Therefore, they will not interfere with the operation of endoscope 11.

The present invention is not limited to the above embodiments, and various changes and modifications may be made within the scope of claims.

What is claimed is:

1. An ultrasonic endoscope, comprising:
   a manipulating portion coupled to a light source device and an ultrasonic observation apparatus through a universal cord;
   an insertion portion insertable into a body cavity;
   a sub-manipulating portion coupled between said insertion portion and said manipulating portion;
   an air-supply path means, a liquid supply path means, and a suction path means in at least said universal cord;
   said insertion portion having a distal end portion;
   said insertion portion including an observation optical system and an ultrasonic vibrator means at said distal end portion thereof;
   balloon means attached to said distal end portion of said insertion portion and surrounding said ultrasonic vibrator means;
   an optical system liquid-supply conduit means at least in said insertion portion for supplying a liquid to said observation optical system for washing said observation optical system;
   a balloon liquid-injection conduit means at least in said insertion portion for injecting said liquid into said balloon means for inflating or expanding said balloon; and
   liquid path switching means selectively and switchably coupling said liquid-supply path means in said universal cord to at least one of said optical system liquid-supply conduit means and said balloon liquid-injection conduit means in said insertion portion.

2. The endoscope of claim 1, wherein said liquid path switching means comprises a liquid path switching cock means coupled to and carried by said sub-manipulating portion, for selectively disconnecting said liquid-supply path means from at least one of said liquid-supply conduit means and said balloon liquid-injection conduit means.

3. The endoscope of claim 2, wherein said insertion portion includes a treatment tool insertion channel means having a distal end opening, and a balloon suction conduit means communicating with said balloon means; and said endoscope further comprises suction switching means for selectively communicating said suction path means with at least one of said treatment tool insertion channel means and said balloon suction conduit means.

4. The endoscope of claim 3, wherein said suction switching means comprises a suction switching cock means coupled to and carried by said sub-manipulating portion, for selectively disconnecting such suction path means from at least one of said treatment tool insertion channel means and said balloon suction conduit means.

5. The endoscope of claim 4, wherein said insertion portion comprises an air supply/liquid supply conduit means, and said manipulating portion comprises an air-supply/liquid-supply valve means, said air-supply/liquid-supply valve means having a piston which is switchable between (i) an air-supply position at which said air-supply path means of said universal cord is communicatingly coupled with said air-supply/liquid-supply conduit means, and said liquid-supply path means of said universal cord is disconnected from said liquid path switching cock means; and (ii) a liquid-supply position at which said air supply path means of said universal cord is disconnected from said air-supply/liquid-supply conduit means, and said liquid supply path means of said insertion portion is in communication with said liquid path switching cock means.

6. The endoscope of claim 5, wherein said manipulating portion comprises suction valve means for selectively causing said suction path means of said universal cord to be in communication with, or to be disconnected from, said suction switching cock means of said manipulating portion.

7. The endoscope of claim 6, wherein said balloon liquid-injection conduit means comprises a syringe mount port means which includes a receiving portion for receiving a syringe thereon, and a check valve.

8. The endoscope of claim 5, wherein said liquid comprises water.

9. The endoscope of claim 2, wherein said insertion portion comprises an air supply/liquid supply conduit means, and said manipulating portion comprises an air-supply/liquid-supply valve means, said air-supply/liquid-supply valve means having a piston which is switchable between (i) an air-supply position at which said air-supply path means of said universal cord is communicatingly coupled with said air-supply-liquid-supply conduit means, and said liquid-supply path means of said universal cord is disconnected from said liquid path switching cock means; and (ii) a liquid-supply position at which said air-supply path means of said universal cord is disconnected from said air-supply/liquid-supply conduit means, and said liquid-supply path means of said insertion portion is in communication with said liquid path switching cock means.

10. The endoscope of claim 9, wherein said liquid comprises water.

11. The endoscope of claim 1, wherein said liquid comprises water

* * * * *